US010746731B2

(12) United States Patent
Vos et al.

(10) Patent No.: US 10,746,731 B2
(45) Date of Patent: Aug. 18, 2020

(54) SURFACE IMMOBILIZATION OF AN ANALYTE-RECOGNIZING MOLECULE

(71) Applicant: IMEC VZW, Leuven (BE)

(72) Inventors: Rita Vos, Baal (BE); Karolien Jans, Tessenderlo (BE); Tim Stakenborg, Heverlee (BE)

(73) Assignee: IMEC VZW, Leuven (BE)

( * ) Notice: Subject to any disclaimer, the term of this patent is extended or adjusted under 35 U.S.C. 154(b) by 10 days.

(21) Appl. No.: 15/577,311

(22) PCT Filed: Jun. 28, 2016

(86) PCT No.: PCT/EP2016/064953
§ 371 (c)(1),
(2) Date: Nov. 27, 2017

(87) PCT Pub. No.: WO2017/001374
PCT Pub. Date: Jan. 5, 2017

(65) Prior Publication Data
US 2018/0149643 A1 May 31, 2018

(30) Foreign Application Priority Data

Jun. 30, 2015 (EP) .................................... 15174655

(51) Int. Cl.
*G01N 33/543* (2006.01)
*G01N 33/531* (2006.01)

(52) U.S. Cl.
CPC ..... *G01N 33/54353* (2013.01); *G01N 33/531* (2013.01); *G01N 33/54386* (2013.01); *B01J 2219/0074* (2013.01); *B01J 2219/00626* (2013.01); *B01J 2219/00637* (2013.01); *B01J 2219/00677* (2013.01); *B01J 2219/00725* (2013.01)

(58) Field of Classification Search
CPC ....... G01N 33/54353; G01N 33/54386; G01N 33/531; B01J 2219/00626; B01J 2219/00677; B01J 2219/00637; B01J 2219/00725; B01J 2219/0074
See application file for complete search history.

(56) References Cited

FOREIGN PATENT DOCUMENTS

| EP | 2 532 639 A1 | 12/2012 |
|---|---|---|
| WO | 2012/079030 A2 | 6/2012 |
| WO | 2012/079030 A3 | 6/2012 |
| WO | 2013/181697 A1 | 12/2013 |
| WO | 2014/056896 A2 | 4/2014 |
| WO | 2014/056896 A3 | 4/2014 |

OTHER PUBLICATIONS

Redeker et al. Protein engineering for directed immobilization. Bioconjugate Chemistry 2013, vol. 24, pp. 1761-1777. (Year: 2013).*
Sun et al. Carbohydrate and protein immobilization onto solid surfaces by sequential diels-alder and azide-alkyne cycloadditions. Bioconjugate Chem. 2006, vol. 17, pp. 52-57. (Year: 2006).*
KeraFAST, Chemoselective ligantion through copper-free click chemistry, Technical note 2012, KeraFAST, Inc. , 27 Drydock, Ave, Boston, MA 02210. (Year: 2012).*
Hapuarachchige et al, Bioorthogonal, two component delivery systems based on antibody and drug-loaded nanocarriers for enhanced internalization of nanotherapeutics., Biomaterials 2014, vol. 35, No. 7, pp. 2346-2354. (Year: 2014).*
Wendeln et al. Orthogonal, metal-free surface modification by strain-promoted azide-alkyne and nitrile oxide-alkene/alkyne cycload-ditions. Chem. Sci. 2012, vol. 3, pp. 2479-2484. (Year: 2012).*
Bélanger, Daniel, et al., "Electrografting: A Powerful Method for Surface Modification", Chem. Soc. Rev., 2011, vol. 40, pp. 3995-4048, DOI:10.1039/c0cs00149j.
Ryken, Jef, et al., "Biosensing With SiO2-Covered SPR Substrates in a Commercial SPR-Tool", Sensors and Actuators B 200, 2014, pp. 167-172.
PCT International Search Report and Written Opinion, PCT International Application No. PCT/EP2016/064953, dated Oct. 13, 2016, 13 pages.
Thermo Scientific: "Crosslinking Handbook", 2012, Thermo Fisher Scientific, pp. 1-54.
Zhao, Yongfeng et al., "Chemoselective Fabrication of High Density Peptide Microarray by Hetero-Bifunctional Tetra (Ethylene Glycol) Linker for Click Chemistry Conjugation", Journal of Biomedical Materials Research, Part A, vol. 100A, No. 1, 2012, pp. 103-110.

(Continued)

*Primary Examiner* — Shafiqul Haq
(74) *Attorney, Agent, or Firm* — McDonnell Boehnen Hulbert & Berghoff LLP (57) ABSTRACT

A method for immobilizing an analyte-recognizing molecule (1) on a surface (2') functionalized with chemical groups $Y^1$ suitable for reacting with a chemical group $X^2$ of a coupling molecule (7) to form a reaction product comprising a chemical group $Y^2$ suitable for reacting with the analyte-recognizing molecule (1), the method comprising the steps of: a) Providing the functionalized surface (2'), b) Contacting the functionalized surface (2') with a solution (6) comprising simultaneously: i) The coupling molecule (7), and ii) The analyte-recognizing molecule (1).

5 Claims, 4 Drawing Sheets

(56) References Cited

OTHER PUBLICATIONS

Kotagiri, Nalinikanth et al., "Antibody Quantum Dot Conjugates Developed via Copper-Free Click Chemistry for Rapid Analysis of Biological Samples Using a Microfluidic Microsphere Array System", Bioconjugate Chemistry, vol. 25, No. 7, 2014, pp. 1272-1281.

Misra, Arvind et al., "Immobilization of Oligonucleotides on Glass Surface Using an Efficient Heterobifunctional Reagent Through Maleimide-Thiol Combination Chemistry", Analytical Biochemistry, vol. 369, 2007, pp. 248-255.

Zhou, Xichun et al., "Improving the Signal Sensitivity and Photostability of DNA Hybridizations on Microarrays by Using Dye-Doped Core-Shell Silica Nanoparticles", Anal. Chem., vol. 76, 2004, pp. 5302-5312.

* cited by examiner

SURFACE IMMOBILIZATION OF AN ANALYTE-RECOGNIZING MOLECULE

The present application is a section 371 U.S. patent application claiming priority to PCT/EP2016/064953, filed Jun. 28, 2016, which claims priority to European Patent Application No. 15174655.9, filed Jun. 30, 2015, the contents of which are hereby incorporated by reference.

TECHNICAL FIELD OF THE INVENTION

The present invention relates to the field of sensors, particularly biosensors for detecting an analyte in a sample. In particular, the present invention relates to a method for immobilizing an analyte-recognizing molecule on a surface of a sensor.

BACKGROUND OF THE INVENTION

In integrated and miniaturized biosensor devices, also called lab-on-chip devices, the biosensor is part of a microfluidic platform that allows for a rapid and automated in-flow detection of the analyte. To ensure optimal sensitivity, a site-selective coupling of the analyte-recognizing molecules or receptors on the sensor area is required.

Different surface chemistries have been tried, mainly self-assembled monolayers of organosilanes, to ensure a covalent binding of the analyte-recognizing molecules to various biosensor devices. For this purpose, silanes with a functional group that is reactive towards the analyte-recognizing molecules, e.g. antibodies, has been used, such as epoxy-silanes. However, these reactive functional groups are prone to hydrolysis and their stability is limited upon storage especially in $H_2O$-containing atmospheres. An alternative, more preferred and widely used approach is to use less reactive groups in combination with a linker group. An example of this approach has been described by J. Ryken et al. (sensors and actuators B 200 (2014) 167-172) and consists in using in a first step, a cross-linker to activate the silane so that it can, in a second step, react with the analyte-recognizing molecule. This is done using a two-step protocol where first the biosensor substrate is activated using the cross-linker followed by the conjugation of the analyte-recognizing molecule in a second reaction.

In order to immobilize the analyte-recognizing molecules on full wafer scale in a cost-effective way, non-contact microarray printing technologies ('spotting') to generate arrays of microdroplets on the area of the biosensor transducer are mostly suited. In order to enable the spotting, both the substrate and the solutions used to spot the analyte-recognizing molecules should be sufficiently stable. Additionally, the two-step approach involves spot-on-spot deposition with an intermediate washing step which is not easy to implement in practice, especially not in a high-throughput environment. There is therefore a need in the art for methods for immobilizing analyte-recognizing molecule on surfaces that overcome or improve on one or more of the above mentioned drawbacks of the prior art.

SUMMARY OF THE INVENTION

It is an object of the present invention to provide good methods, solutions and kits of parts for immobilizing an analyte-recognizing molecule on a surface.

It is an advantage of embodiments of the present invention that the immobilization of an analyte-recognizing molecule on a functionalized surface can performed in a single step, thereby easing the manufacture.

It is an advantage of embodiments of the present invention that reactive groups more reactive than —SH or —$NH_2$ are not introduced in the analyte-recognizing molecule before it is being immobilized on the surface, thereby assuring the stability in time of the analyte-recognizing molecule prior to its immobilization on the functionalized surface.

It is an advantage of embodiments of the present invention that the coupling molecules are not contacted with the surface or the analyte-recognizing molecule until just before the analyte-recognizing molecule is contacted with the surface. This promotes the stability in time of the surface and of the analyte-recognizing molecule.

It is an advantage of embodiments of the present invention that the single-step method of the present invention provides good control over the immobilization process and conservation of the analyte detection ability (typically by conserving the biological activity of the analyte-recognizing biomolecule).

It is an advantage of embodiments of the present invention that it represents an excellent single step alternative to the two-steps methods of the prior art, with comparable control and analyte detection ability.

It is an advantage of embodiments of the present invention that the functionalized surface, prior to immobilization of the analyte-recognizing molecule, can be stable over long periods.

It is an advantage of embodiments of the present invention that the immobilization of the analyte-recognizing molecule on the surface is very stable, especially when it is covalent.

It is an advantage of embodiments of the present invention that uniform, dense arrays of small droplets of the analyte-recognizing molecule can be easily spotted in one step via non-contact microarray printing. A two steps method has the drawback of possible bad overlap between successive spotting steps and for accurate spot-on-spot printing, a good alignment is required. In addition, a two steps method necessitates an intermediate washing step.

The above objective is accomplished by a method and device according to the present invention.

In a first aspect, the present invention relates to a method for immobilizing an analyte-recognizing molecule on a surface functionalized with chemical groups $Y^1$ suitable for reacting with a chemical group $X^2$ of a coupling molecule to form a reaction product comprising a chemical group $Y^2$ suitable for reacting with the analyte-recognizing molecule, the method comprising the steps of:
  a. Providing the functionalized surface,
  b. Contacting the functionalized surface with a solution comprising simultaneously:
    i. The coupling molecule, and
    ii. The analyte-recognizing molecule.

In a second aspect, the present invention relates to a solution comprising simultaneously:
  i. a coupling molecule having a chemical group $X^2$ suitable for reacting with a chemical group $Y^1$ of a surface to form a reaction product comprising a chemical group $Y^2$ suitable for reacting with an analyte-recognizing molecule, and
  ii. the analyte-recognizing molecule.

In a third aspect, the present invention relates to a kit of parts comprising:
  a. a first solution comprising a coupling molecule having a chemical group $X^2$ suitable for reacting with a chemical group Y1 of a surface to form a reaction product comprising a chemical group $Y^2$ suitable for reacting with an analyte-recognizing molecule, and, b. a second solution comprising the analyte-recognizing molecule, wherein the first and the second solution are such that once mixed together they form a solution comprising:

the coupling molecule at a concentration at least equal to 1 µM and at most equal to 1 mM, the analyte-recognizing molecule at a concentration at least equal to $1*10^{-12}$, preferably at least equal to $1*10^{-8}$ mol/l.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of methods and devices in this field, the present concepts are believed to represent substantial new and novel improvements, including departures from prior practices, resulting in the provision of more efficient and reliable methods and devices of this nature.

The teachings of the present invention permit the design of improved methods and apparatus for immobilizing an analyte-recognizing molecule on a surface.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "coupled", also used in the claims, should not be interpreted as being restricted to direct connections only. The terms "coupled" and "connected", along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following term is provided solely to aid in the understanding of the invention.

As used herein and unless provided otherwise, the term "analyte" refers to an element (typically a chemical compound) that can be detected in an assay by binding to the analyte-recognizing molecule. This binding is selective and preferably specific. Therefore, the analyte can be for instance, and without limitation, any substance for which there exists a naturally occurring antibody or for which an antibody can be prepared. The analyte could be, but is not limited hereto, a complementary nucleic acid strand (DNA, PNA, RNA), a hapten, a carbohydrate, a lipid, a cell, a protein an hormone, an antibiotic, an antibody, an antigen, an enzyme, a drug or a drugs of abuse.

The invention will now be described by a detailed description of several embodiments of the invention. It is clear that other embodiments of the invention can be configured according to the knowledge of persons skilled in the art without departing from the technical teaching of the invention, the invention being limited only by the terms of the appended claims.

In the first aspect, the invention relates to a method for immobilizing an analyte-recognizing molecule on a surface.

This immobilizing can be achieved by any type of chemical bonding such as a covalent bonding, an electrostatic bonding, a hydrogen bridge bonding or a combination thereof. Preferably, the immobilizing may be achieved by covalent bonding.

The analyte-recognizing molecule is a molecule that interacts with an analyte, and preferably binds an analyte, with selectivity and preferably with specificity.

In embodiments, the analyte-recognizing molecule may be a first biomolecule such as a protein. Preferably, the analyte-recognizing molecule is a protein. For instance, the protein can be an antibody or an enzyme. In the case of an antibody, the analyte can be an antigen specific to that antibody. In the case of an enzyme, the analyte can be a substrate specific to that enzyme.

In embodiments, the analyte-recognizing molecule may be a bio-recognition molecule, i.e. the analyte may be a biomolecule.

In embodiments, the analyte-recognizing molecule may comprise at least one —$NH_2$, —SH, —COOH, —OH, aldehyde or ketone, or phosphate or pyrophosphate group and the coupling molecule may be suitable for reacting with the —$NH_2$, —COOH, —OH, aldehyde or ketone, or phosphate or pyrophosphate group respectively. Preferably, the analyte-recognizing molecule may comprise at least one —$NH_2$ or —SH.

In embodiments where the analyte-recognizing molecule has a —$NH_2$ group, $Y^2$ may be selected from the group consisting of o-acylisourea, N-group, hydroxysuccinimide ester, isothiocyanate, isocyanate, acyl azide, sulfonylchoride, aldehyde, oxirane, carboxyl, carbonate, arylating agents, imidoester, acid anhydride, fluorophenyl ester, and hydroxymethyl phosphine derivative.

In embodiments, where the analyte-recognizing molecule has a —SH group, $Y^2$ may be selected from the group consisting of activated halogens (e.g. haloacetyls, benzyl halides and alkyl halides), maleimide, aziridine, acryloyl, vinylsulfone, arylating agent and disulfide (e.g. pyridyl disulfide).

In embodiments, where the analyte-recognizing molecule has a —COOH group, $Y^2$ may be selected from the group consisting of diazoalkane and diazoacetyl.

In embodiments, where the analyte-recognizing molecule has an aldehyde or ketone group, $Y^2$ may be selected from the group consisting of hydrazide and —$NH_2$.

In embodiments, where the analyte-recognizing molecule has a phosphate or a pyrophosphate group, $Y^2$ may be a carbonyldiimidazole (e.g. for reaction with —$NH_2$).

Among activated halogens, the relative reactivity is I>Br>Cl>F with F being almost unreactive.

Arylating agents are reactive aromatic compounds containing a reactive replaceable group on the ring that can undergo nucleophilic aromatic substitution. This reactive replaceable group is typically a halogen or a sulfonate group. The presence of electron withdrawing groups (e.g. nitro) on the ring increases the reactivity of the reactive replaceable group. The relative rate of reactivity for reactive replacable groups in arylating agents is F>Cl, Br>Sulfonate.

Preferably, $Y^2$ is N-hydroxysuccinimide ester.

The $Y^2$ group is preferably selected so that its reactivity toward the analyte-recognizing molecule is lower than the reactivity of $X^2$ toward $Y^1$. This limits the number of coupling molecules that reacts with each analyte-recognizing molecule, thereby preserving the affinity of the analyte-recognizing molecule for the analyte.

The solution comprising the analyte-recognizing molecule and the coupling molecule may further comprise a stabilizing agents.

Examples of compounds that can be added to the analyte-recognizing molecule to extend the stability are for instance cryoprotectants such as glycerol or ethylene glycol to prevent formation of ice crystals at −20° that destroy the protein structure; protease inhibitors such as phenylmethylsulfonyl fluoride, benzamidine, Petstatin A, Leupeptin, Aprotinin, Antipain, EDTA and EGTA to prevent proteolytic cleavage of proteins; anti-microbial agents such as $NaN_3$ or thimerosal to inhibit microbial growth; metal chelators such as EDTA to avoid metal induced oxidation of —SH groups; reducing agents such as dithiothreitol (DTT) and 2-mercaptoethanol (2-ME) to maintain the protein in the reduced state; polyols and sugars such as glycerol, erythritol, arabitol, sorbitol, mannitol, xylitol, mannisdomannitol, glucosylglycerol, glucose, fructose, sucrose, threhalose, isofluoroside to stabilize hydration shells and protect against aggreagation; polymers such as dextrans, levans and polyethyleneglycol to prevent protein aggregation; amino acids and derivatives such as glycine, alanine, proline, taurine, betaine, octopine, glutamate, sarcosine, γ-aminobutyric acid, trimethylamine N-oxide; salts with large anions at low concentrations such as citrate, sulfates, acetate, phosphates, and quaternary amines.

Stabilizing agents might be commercially available solutions (e.g. from Surmodics, Gwent Group) comprising components listed above or other formulations.

The sample comprising the analyte is typically a fluid comprising the analyte. In embodiments, the fluid is a gas or a liquid. Preferably it is a liquid. Preferably it is an aqueous solution. Preferably it is a biological liquid such as blood, serum or urine.

The surface is typically a surface of a substrate.

In embodiments, the substrate may be an inorganic substrate selected from the group consisting of a metal, a metal oxide, a metal nitride, a metal oxynitride, a metalloid, a metalloid oxide, a metalloid nitride, a metalloid oxynitride and a metalloid carbide.

The inorganic substrate is preferably selected from the group consisting of Si, $SiO_2$, $Si_3N_4$, SiC, $SiO_xN_y$, $Al_2O_3$, AlN, $TiO_2$, TiN, TiC, TiCN, $Ta_2O_3$, TaN, TaC, TaCN, $ZrO_2$, $HfO_2$, HfSiO, HfSiON, ZrSiO, ZrSiON, HfN, Au, Pt, Pd, Ru and Cu, wherein x is from 0 to 2. Wherein y is from 0 to 1.33.

When the chemical groups $Y^1$ are introduced by silanes and when these substrates do not have reactive oxygen species on their surface, these surfaces are preferably hydroxylated to allow the reaction with the silanes.

In embodiments, the substrate may be coated with an organic polymeric layer or may be an organic substrate such as a polymeric substrate. For instance, the polymeric substrate or the polymeric layer could be made of polymers having $Y^1$ side chains and/or end groups.

In embodiments, the surface may be part of a microfluidic system.

In embodiments, the surface may be the bottom or top of a microfluidic channel. The method of the first aspect is especially useful for immobilizing analyte-recognizing molecules in a microfluidic channel in a microfluidic device. Microfluidic devices comprise microfluidic channels of small dimensions and it is advantageous to immobilize analyte-recognizing molecules at very specific locations before (or after) forming the sidewalls of the channels. The contacting step of the method of the first aspect consisting in a single step, it simplifies this immobilization.

In embodiments, the surface may be shaped such that it forms a microfluidic channel, a microwell, a reservoir, or at least part thereof.

In a nutshell, the method according to the present invention can be integrated in a method for forming a microfluidic biosensor comprising the steps of coupling a transducer to a surface, patterning channels (e.g. micro-channels) which bottom comprises said surface, immobilizing analyte-recognizing molecules on said surface via a method according to any embodiment of the first aspect, and providing a cover on top of said channels. Further steps to finalize the device are bonding, dicing and packaging the device.

Microfluidics design is well known by the person skilled in the art, and is therefore not further discussed in detail.

In embodiments, the surface may be coupled with a transducer for generating a readable signal output upon interaction (e.g. binding) of an analyte with the immobilized analyte-recognizing molecule. The combined presence of the surface with analyte-recognizing molecules immobilized thereon and of the transducer form the major elements of a sensor permitting the detection of the analyte.

The surface is functionalized with chemical groups $Y^1$ suitable for reacting with a chemical group $X^2$ of a coupling molecule (7).

In embodiments, the functionalization of the surface with chemical groups $Y^1$ may be performed on the full surface of a wafer.

In embodiments, the surface functionalized with chemical groups $Y^1$ may be composed of a surface overlaid by a layer formed from at least one first molecular species comprising the chemical group $Y^1$.

In embodiments, the layer may be a self-assembled layer.

In embodiments, the layer may be a monolayer, preferably a self-assembled monolayer. A multilayer is of course also possible but since what is needed for the method is the presence of the chemical groups $Y^1$ on the surface, a mono layer is sufficient and preferable in order not to take too much space. This is especially interesting in microfluidics where space for flowing fluid in channels should not be reduced too much.

In embodiments, the layer (multilayer or monolayer) may have a thickness of up to 10 µm but preferably it has a thickness of at most 10 nm. This is advantageous in microfluidic applications where the layer should not reduce too much the space available for the fluid to flow. Preferably, for certain sensors such as optical sensors or others, the layer may have a thickness of from 0.5 to 5 nm.

Various methods can be used to provide the layer. Monolayers are best provided by self-assembly via dip coating in a solution comprising the first molecular species comprising the chemical group $Y^1$. Thicker layers can for instance be provided by spin coating of such a solution. The solution is typically a 1-10% solution in a solvent. Examples of typical solvents are toluene, THF, cyclohexane and benzene.

In embodiments, the functionalization of the surface with $Y^1$ functional groups can be performed by vapor phase deposition. In this deposition method, vapors of the first molecular species can be generated by heat and/or low pressure, then deposited on the surface. Such a vapor phase coating is preferred to a solution coating because it is better controlled and more efficient. However, if the first molecular species cannot be volatized, a solution based method can of course be used.

In addition, the functional groups $Y^1$ can also be introduced by electrografting, e.g. reduction of diazoniumsalts on conducting surfaces, grafting of alkynes on Si—H, but also other reactions are possible (see e.g. Bilanger and Pinson, Chem. Soc. Rev. 40, 3995-4048 (2011)).

In embodiments, step a of the method may comprise the steps of:
   a1. Providing a bare surface,
   a2. Contacting the bare surface with a first composition comprising the at least one first molecular species, the at least one first molecular species comprising the chemical group $Y^1$, as well as a chemical group $X^1$ suitable for attaching the at least one first molecular species to the bare surface.

In embodiments, the at least one first molecular species may be of general formula $X^1$—R—$Y^1$, wherein R is a spacer such as an organic radical, straight or branched, saturated or unsaturated. Preferably, R is a straight unsaturated organic radical.

In embodiments, R may comprise phenylene or alkene groups. This is advantageous for instance when the surface belong to an electrochemical sensor.

In embodiments, R may consist of from 3 to 400 atoms, preferably from 3 to 320 atoms, more preferably from 3 to 250 atoms, yet more preferably from 3 to 80 atoms, and most preferably from 30 to 80 atoms. Preferably, these atoms are selected from carbon, hydrogen and oxygen.

In embodiments, $X^1$—R—$Y^1$ may have the structural formula $X^1$—$(R^1)_q$—$(O[CH_2]_tCH_2)_m$—O—$(CH_2)_o$—$Y^1$ or $X^1$—$(R^1)_q$—$(O[CH_2]_tCH_2)_m$—$(CH_2)_o$—$Y^1$, preferably $X^1$—$(R^1)_q$—$(O[CH_2]_tCH_2)_m$—O—$(CH_2)_o$—$Y^1$.

o is an integer from 0 to 30, preferably from 0 to 3, and most preferably o is 0.

m is an integer from 0 to 15000, preferably from 1 to 1250, more preferably from 2 to 1000, from 3 to 500, from 3 to 100, from 3 to 50, from 3 to 30, from 3 to 20, from 3 to 15, from 3 to 10, from 3 to 8. Alternatively, m is an integer from 0 to 30, from 1 to 20, from 1 to 15, from 1 to 10, from 1 to 8, or from 1 to 6. In embodiments, m may be 0. In some embodiments, both m and o are 0.

q is 0 or 1.

t is 1 or 2 and is preferably 1.

$R^1$ is preferably selected such that a stable ordered monolayer is formed.

$R^1$ preferably promote the formation of a self-assembling monolayer and can be a organic chain, e.g. a hydrocarbylene group. The organic group can include n carbon atoms, n being an integer higher (or equal to) 1, 3, 6, 8, or 10, preferably from 1 to 30 and more preferably from 3 to 30. $R^1$ can also represent a hydrocarbyl group interrupted by a —CO— (ketone), —CONH, —CONHCO—, —CSNH—, —CS—, and the like. For instance the hydrocarbylene group can optionally comprise one or more carboxy groups in the main chain of the hydrocarbylene group. The hydrocarbylene group can also be interrupted by one or more heteroatoms. The heteroatom can be selected from the group consisting of —N—, —O—, and —S—. In particular, the heteroatom can be O. For instance, $R^1$ can comprise one or more heteroatoms in the main chain of the hydrocarbylene group. The organic group can also be branched. $R^1$ can include a first part which is a hydrocarbonylene group and a second part which is a hydrocarbylene group interrupted by a heteroatom such as oxygen.

In an advantageous embodiment, $R^1$ may be or comprise an alkyl chain —$(CH_2)_n$—, n being an integer from 1 to 30 and preferably from 3 to 30, for instance from 3 to 25, preferably from 3 to 20, e.g. from 5 to 20, or from 8 to 16 or from 10 to 16.

In a preferred embodiment, $R^1$ may be a saturated or ethylenically unsaturated hydrocarbylene group with 1 to 30 carbon atoms (preferably with 3 to 30 carbon atoms) selected from the group consisting of alkyl, alkenyl, cycloalkyl, cycloalkyl-alkyl, cycloalkenyl, cycloalkenylalkyl and cycloalkylalkenyl, said group optionally comprising one or more heteroatoms selected from nitrogen, oxygen and sulfur in the main chain, and said group optionally comprising one or more oxo substituents.

In embodiments, $X^1$—R—$Y^1$ may be $X^1$—$(CH_2)_n$—$(OCH_2CH_2)_m$—O—$(CH_2)_o$—$Y^1$ or $X^1$—$(CH_2)_n$—$(OCH_2CH_2)_m$—$(CH_2)_o$—$Y^1$ and preferably $X^1$—$(CH_2)_n$—$(OCH_2CH_2)_m$—O—$(CH_2)_o$—$Y^1$ wherein m, n and o are integers independently selected in the range going from 0 to 30 wherein at least one of m and n is above 0.

In embodiments, n may be from 8 to 13.

In embodiments, m may be from 6 to 9. Such m values typically give the best compromise between space occupancy of the layer formed of the first molecular species and the solubility of the first molecular species.

In embodiments, o may be equal to 0.

In embodiments, step b may comprise contacting the bare surface with a vapour of the at least one first molecular species.

In embodiments, the at least one first molecular species may comprise at least two first molecular species having different lengths. This is advantageous as it improves the anti-fouling properties of the coating.

In this last embodiment, the at least two first molecular species may have the same n but different m.

In embodiments, $X^1$ may be selected from the group consisting of $X^1a$, $X^1b$ and $X^1c$, wherein $X^1a$ is selected from the group consisting of —$SiZ_x(CH_3)_y$, in which Z is selected from the group consisting Cl, $OCH_3$ and $OCH_2CH_5$ and with y=0, 1 or 2 and x=3-y, —COOH, —$PO(OH)_2$, —$NH_2$, wherein * indicates the point of attachment with the Si atom, $X^1b$ is —SH or —SeH, and $X^1c$ is selected from the group consisting of —CH=$CH_2$ and —C≡CH, Wherein if $X^1$ is $X^1a$, the bare surface comprises OH groups (reactive toward $X^1a$), Wherein if $X^1$ is $X^1b$, the bare surface is a metal surface, Wherein if $X^1$ is $X^1c$, the group $Y^1$ is not —$N^3$ and the bare surface comprises Si—H groups.

$Y^1$ is preferably selected so that it more readily reacts with $X^2$ than with the analyte-recognizing molecule (e.g. the —$NH_2$ and/or —SH groups of that molecule). Preferably, $Y^1$ does not directly react with the analyte-recognizing molecule. Aldehyde for $Y^1$ is therefore not preferred.

In embodiments, $Y^1$ may be selected from the group consisting of —$N_3$, alkyne, and —COOH wherein If $Y^1$ is —$N_3$, $X^2$ is an alkyne which is strained or not, and if the alkyne is not strained, step b is performed in presence of a catalyst suitable for enabling the reaction of an alkyne, which is not strained, with —$N_3$, if $Y^1$ is an alkyne which is strained or not, $X^2$ is —$N_3$, and if the alkyne is not strained, step b is performed in presence of a catalyst suitable for enabling the reaction of an alkyne, which is not strained, with —$N_3$, if $Y^1$ is —COOH, $X^2$ is either a carbodiimide or a diazo group =$N_2$.

—$N_3$ groups have the advantage to be very stable and to provide therefore a very stable surface.

—COOH are less preferred.

Suitable catalyst are copper based catalysts. Both Cu(I) and Cu(II) catalysts are suitable. Cu(I) catalysts are preferred. In general, the amount of the Cu(I) or Cu(II) catalyst will range from 0.01% to 5% by weight of the alkyne and azide containing compounds. The Cu(I) catalyst might be provided by adding Cu(II) species and a reducing agent such as ascorbate.

In embodiments, the binding reaction rate between $Y^1$ and $X^2$ may be higher than the binding reaction rate between $Y^2$ and the analyte-recognizing molecule.

In an embodiment, $Y^1$ may be —COOH, $X^2$ may be a carbodiimide, and $Y^2$ may be o-acylisourea. When $X^2$ is a carbodiimide, the coupling molecule typically only comprises the group $X^2$, the group $Y^2$ being formed only after the reaction of $X^2$ with $Y^1$. As a result, this coupling molecule enables the attachment of the analyte-recognizing molecule but it is not present in the final reaction product. It therefore does not introduce a spacer between the functionalized surface and the analyte-recognizing molecule. This is explained in the reaction scheme below:

Wherein $R_1$—COOH represents the functionalized surface and wherein $R_2$—$NH_2$ represents the analyte-recognizing molecule. Before that the reaction product of the functionalized surface and the carbodiimide reacts with the $R_2$—$NH_2$, it is possible to react that reaction product with N-hydroxysuccinimide (NHS), thereby forming an NHS-ester that can now react with $R_2$—$NH_2$.

An advantage of such a selection of $Y^1$ and $X^2$ groups is that the reaction of the $Y^2$ (o-acylisourea) of the reaction product and the —$NH_2$ of the analyte-recognizing molecule cannot occur before the reaction of $Y^1$ and $X^2$.

For instance, $Y^1$ may be —COOH and the coupling molecule may be 1-ethyl-3-(3-dimethylaminopropyl)carbodiimide or a salt thereof.

In embodiments, $Y^1$ may be —$N_3$ and $X^2$ may be an alkyne group of a cycloalkyne. This is advantageous because the alkyne group in a cycloalkyne is typically strained, which makes it more reactive than a non-strained cycloalkyne. As a consequence, this strained alkyne can react with a —$N_3$ group without the need for a catalyst. An example of cycloalkyne is given in the formula:

wherein: each $R^1$ is independently selected from the group consisting of hydrogen, halogen, hydroxy, alkoxy, nitrate, nitrite, sulfate, and a $C_1$-$C_{10}$ organic group; each $R^2$ is independently selected from the group consisting of hydrogen, halogen, hydroxy, alkoxy, nitrate, nitrite, sulfate, and a $C_1$-$C_{10}$ organic group; wherein X can be a carbon or a nitrogen group connected to the $Y^2$ group via a linker. A specific example is DBCO-PEG4-NHS (Jena Bioscience, Germany) used in the examples.

An advantage of such a selection of $Y^1$ and $X^2$ groups is that the reaction of $Y^1$ and $X^2$ will typically be faster than the reaction of $Y^2$ with the —$NH_2$ or the —SH of the analyte-recognizing molecule.

In embodiments, $X^2$ and $Y^2$ are selected in such a way that $X^2$ reacts more readily with $Y^1$ than with $Y^2$. This permits to avoid polymerization of the coupling molecule.

In a preferred embodiment, $Y^1$ is —$N_3$, $X^2$ is a strained alkyne, and $Y^2$ is N-hydroxysuccinimide ester. This embodiment has the advantages of a stable —$N_3$ functionalized surface and a reaction rate between $X^2$ and $Y^1$ higher than between $Y^2$ and the —$NH_2$ of the analyte-recognizing molecule.

In embodiments, the solution may be at a pH from 4 to 9. The optimal pH depends on the type of cross-linker used. For the cross-linker used in the examples, the pH is preferably 5-9, and more preferably 5-7.

In embodiments, the solution has an ionic strength of from 0.01 to 0.5 M.

In embodiments, the solution may further comprise a buffering compound. For instance, the buffering compound may be a sodium acetate/acetic acid buffer.

In embodiments, the buffering compound may be free of primary or secondary amino groups.

In embodiments, the solution may be aqueous. A preferred embodiment is an aqueous solution at pH 4-9, ionic strength of from 0.01 to 0.5M and comprising a buffering compound.

In embodiments, the solution may comprise a uniformity agent. Examples of uniformity agent are betaïne, polyols (e.g. glycerol), sugars (e.g. trehalose), and surfactants (e.g. Tween-20).

In embodiments, the solution may comprise the coupling molecule at a concentration at least equal to 1 µM.

In embodiments, the solution may comprise the coupling molecule at a concentration of at most 1 mM, preferably at most 100 µM, more preferably at most 10 µM.

In embodiments, the analyte-recognizing molecule may be present in the solution at a concentration at least equal to $1*10^{-12}$, preferably at least equal to $1*10^{-8}$ mol/l.

In embodiments, the solution may comprise the analyte-recognizing molecule and the coupling molecule may be prepared by mixing the analyte-recognizing molecule and the coupling molecule at most 3 hours, preferably at most 1 hour and most preferably at most 30 min before step b.

In embodiments, the coupling molecule may have the general formula $X^2$—$R^2$—$Y^2$ wherein $R^2$ is an organic group, branched or not, saturated or not, comprising from 1 to 30 carbon atoms, optionally comprising one or more heteroatoms selected from the group consisting of —N—, —O—, and —S—, and optionally comprising one or more oxo substituents.

In embodiments, $R^2$ may be defined as R is defined in any embodiment.

In embodiments, the coupling molecule may have the general formula $X^2$—$(CH_2)_n$—$(OCH_2CH_2)_m$—O—$(CH_2)_o$—$Y^2$ wherein n is an integer from 0 to 30 and preferably from 0 to 10, m is an integer from 0 to 15000, preferably from 0 to 10, o is an integer from 0 to 30, preferably 0 to 10 wherein n+m+o is at least equal to 1.

In embodiments, m may be from 1 to 10, preferably from 2 to 6. Having m in that range may help to solubilize the coupling molecule.

In embodiments, step b may comprise the deposition on the functionalized surface of a drop (preferably having a drop size of from 1 pL to 2000 pL) of the solution. For instance, step b may comprise a non-contact microarray printing step. With certain advanced spotting tools, small volumes of solution ($10^{-15}$-$10^{-18}$ L) can be deposited via a direct writing process using an AFM-like tip.

The deposition of the solution by means of drops is currently the most preferred way to introduced analyte-recognizing molecules on a surface comprised in a microfluidic device. The present invention is particularly advantageous when the deposition is performed by way of drops. Indeed, it is particularly difficult to use a two-step drop-mediated deposition wherein the second drop must be deposited exactly where the first drop was deposited and where a washing step is needed between the first and the second drop. In the present invention, since step b is performed in a single step there is no need for the second drop.

Alternatively, step b may comprise a step of flowing the solution across the surface. If the surface is comprised in the bottom or top of a channel of a fluidic device, step b may comprise flowing the solution in the channel.

In embodiments, a blocking agent may be introduced either after (or during) the functionalization of the surface with $Y^1$ chemical groups or preferably after (or during) the immobilization of the analyte recognizing molecule. The presence of a blocking agent is advantageous because it prevent loss of analyte and non-specific bonding of the analyte with the surface.

This blocking agent is introduced before contact of the surface bearing the analyte-recognizing molecules with the analyte. Alternatively, it might be introduced also together with the analyte in the same step. This permits to cover any part of the surface that has no analyte-recognizing molecules thereon, thereby reducing the extent of non-selective or of non-specific interactions between the analyte and the surface away from the analyte-recognizing molecules. Examples of suitable blocking agents are bovine serum extracts such as Assay Diluent (a phosphate buffered saline solution containing bovine serum), bovine serum albumin (BSA), and compounds comprising a $X^2$ group and polyethylene glycol groups (e.g. DBCO-PEG4-OH or DBCO-PEG 5 kDa). By preference, they should at least be 6 ethyle glycol-units present.

In a second aspect, the present invention relates to a solution comprising simultaneously:
 i. a coupling molecule having a chemical group $X^2$ suitable for reacting with a chemical group $Y^1$ of a surface to form a reaction product comprising a chemical group $Y^2$ suitable for reacting with an analyte-recognizing molecule, and
 ii. the analyte-recognizing molecule.

In embodiments, the coupling molecule and the analyte-recognizing molecule may independently be as defined in any embodiment of the first aspect.

In a third aspect, the present invention relates to kit of parts comprising:
 a. a first solution comprising a coupling molecule having a chemical group $X^2$ suitable for reacting with a chemical group $Y^1$ of a surface to form a reaction product comprising a chemical group $Y^2$ suitable for reacting with an analyte-recognizing molecule, and,
 b. a second solution comprising the analyte-recognizing molecule,
wherein the first and the second solution are such that once mixed together they form a solution (6) comprising:
 the coupling molecule (7) at a concentration at least equal to 1 μM and at most equal to 1 mM,
 the analyte-recognizing molecule (1) at a concentration at least equal to $1*10^{-12}$, preferably at least equal to $1*10^{-8}$ mol/l.

In embodiments, the coupling molecule, the analyte-recognizing molecule, and the solution in which both components are mixed may independently be as defined in any embodiment of the first aspect.

In embodiments, the kit of parts may further comprise a sensor for the detection of an analyte in a sample fluid, the sensor comprising:
 i. the surface functionalized with chemical groups $Y^1$ and suitable for immobilizing the analyte-recognizing molecule by reacting the chemical groups $Y^1$ with the coupling molecule to form the reaction product suitable for reacting with the analyte-recognizing molecule, and
 ii. a transducer coupled with the functionalized surface and suitable for generating a readable signal output upon interaction of the analyte with the immobilized analyte-recognizing molecule.

In embodiments, the surface may be as defined in any embodiment of the first aspect.

In embodiments, the sensor may be a biosensor.

In embodiments, the sensor may be a microfluidic device and the surface may be comprised in the bottom of a microfluidic channel.

In embodiments, the transducer may be coupled to a signal and data processor to transform the readable signal output into information that can be conveyed to and interpreted by a human operator.

A further aspect of the present invention relates to a device comprising a analyte-recognizing molecule immobilized on a surface thereof, wherein immobilization of the analyte-recognizing molecule on the surface is obtained by the method as defined in the first aspect.

In yet a further aspect, the present invention relates to a sensor for the detection of an analyte in a sample fluid, the sensor comprising:
 i. a device as defined in the previous aspect and
 ii. a transducer coupled with the surface and suitable for generating a readable signal output upon interaction of an analyte with the immobilized analyte-recognizing molecule.

According to a preferred embodiment, the sensor is suitable for determining the presence of the analyte in a sample. The sensor can be arranged such that it acts as a biosensor chip (Surface Plasmon Resonance SPR chip, Surface Acoustic Wave SAW chip, . . . ).

In embodiments, the surface may be a surface of the transducer. The transducer can be part of, but is not limited hereto, a Surface Plasmon Resonance sensor, Surface Acoustic Wave sensors, Quartz Crystal Microbalance, Amperometric sensors, optical sensors, Capacitive sensors, Interdigitated Electrodes or ChemFET sensors. An example of transducer is a plasmon reasonance set up. This is the transducer used in the examples of the present invention. Another example of transducer is interdigitated electrodes comprising the surface on which the analyte-recognizing molecules are immobilized.

In yet a further aspect, the present invention relates to a method for detecting the presence of an analyte in a sample comprising contacting the sample with the surface as defined in any embodiment of the present invention.

In yet a further aspect, the present invention relates to the use of the device or sensor as defined in any embodiment of the present invention for detecting the presence of an analyte in a sample.

Figure 1:
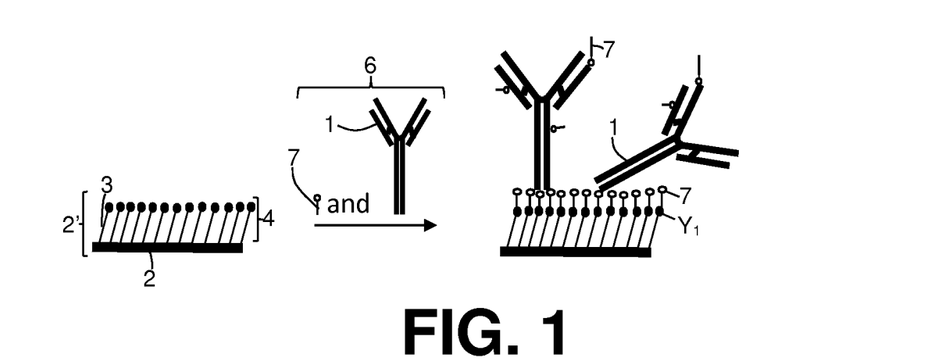
FIG. 1 is a schematic representation of a method for immobilizing an analyte-recognizing molecule according to an embodiment of the present invention.

FIG. 1 shows a scheme of a method according to an embodiment of the present invention. On the left side of FIG. 1, a surface (2') is depicted on which chemical groups $Y^1$ are present. The chemical groups $Y^1$ belong to first molecular species (3). The first molecular species (3) form a self-assembled monolayer (4) on the surface (2'). The surface (2') functionalized with $Y^1$ chemical groups is then contacted with a solution (6) comprising simultaneously a coupling molecule (7) and an analyte-recognizing molecule (1) (here an antibody (1)). The result of this contacting step is depicted on the right side of FIG. 1 where the functionalized surface (2') is shown to have reacted with coupling molecules (7), some of the coupling molecules (7) having further reacted with the antibody (1).

In the following examples, surface plasmon resonance (SPR) sensitivity measurements were performed on a Biacore3000 system (GE Healthcare, United Kingdom). SPR reflectance dip positions are automatically converted into arbitrary response units (RU).

EXAMPLE 1

Proof of Concept and Evaluation of the Optimal Concentration of Coupling Molecule (7)

$SiO_2$-covered Au substrates were prepared and cleaned as described in J. Fyken et al. (sensors and actuators B 200 (2014) 167-172). After the cleaning, the $SiO_2$-covered Au substrates were transferred to a vapor phase deposition tool. The substrat was heated until 140 deg C. at 25 mbar together with 100 ul of the silane. This allows the silane to evaporate and react with the surface during 1 hour, thereby providing a substrate comprising a functionalized surface (2'). These substrates were then separated into a first substrate (Sc) and a set of substrates (Sx). The first substrate (Sc) was used to perform a comparative example. The set of substrates (Sx) was used to perform an embodiment of the present invention.

Figure 2:
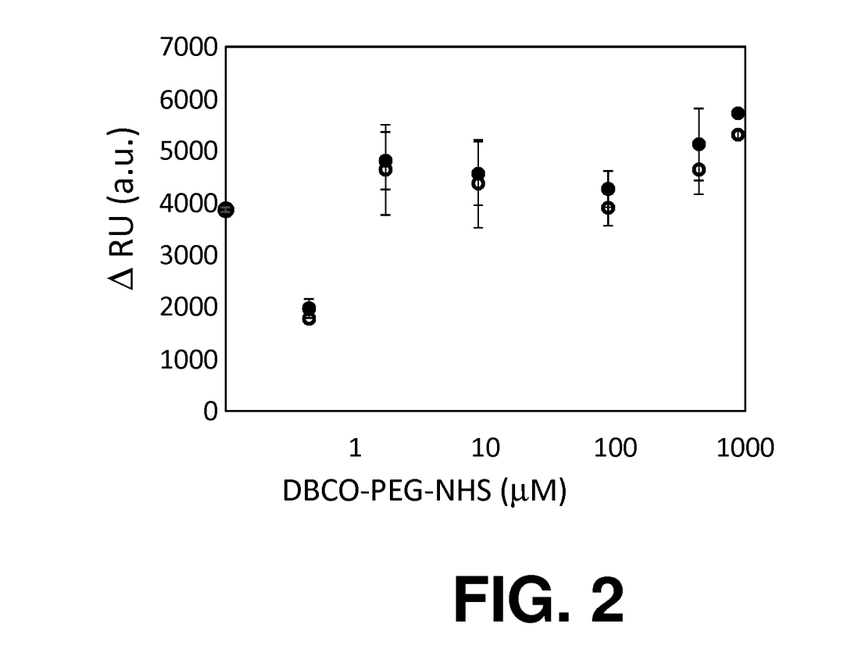
FIG. 2 is a graph of the SPR signal obtained after immobilization of analyte-recognizing molecules as a function of the coupling molecule concentration in embodiments of the present invention.

The functionalized surface (2') of the first substrate (Sc) was treated as follow. The immobilization of the capture antibodies (1) was performed in the Biacore 3000 tool at a temperature of 20° C. After docking the first substrate (Sc), a priming step with phosphate buffered saline (PBS) running buffer (150 mM NaCl, 50 mM potassium phosphate, pH 7.4) was conducted. Prior to immobilization, the functionalized surface (2') of the substrate (Sc) was activated with an injection of 50 μl DBCO-PEG4-NHS (7) (Jena Bioscience, Germany) in $EtOH/H_2O$ (1/1) at a flow rate of 5 μl/min. DBCO-PEG4-NHS (7) has the following chemical formula:

In a subsequent step, 150 μl of the anti-PSA antibody (1) solution (Fujirebio Diagnostics, Pennsylvania, USA) (250 μg/ml in 15 mM acetate buffer, pH 5.5) was injected at the same flow rate. Two short pulses of glycine/HCl (5 μl, 10 mM, pH 2.2) were used to remove non-covalently bonded antibodies from the surface (2'). The measured difference in SPR signal between the functionalized surface (2') and the surface (2') after anti-PSA immobilization is shown in FIG. 2 (black spot on the Y-axis). This signal obtained in the comparative two-step protocol above will be our reference point.

The functionalized surface (2') of each substrate of the set (Sc) was treated as follow. As in the case of the comparative example, the immobilization of the capture antibodies (1) was performed in the Biacore 3000 tool at a temperature of 20° C. For each substrate (Sx), after docking, a priming step with phosphate buffered saline (PBS) running buffer (150 mM NaCl, 50 mM potassium phosphate, pH 7.4) was conducted. Prior to immobilization, the functionalized surface (2') of each substrate (Sx) was contacted with a 200 μl injection at a flow rate of 5 μl/min of the anti-PSA antibody solution (250 μg/ml in 15 mM acetate buffer, pH 5.5) to which a different concentration of DBCO-PEG4-NHS (7) was added for each substrate (Sx). The concentrations in DBCO-PEG4-NHS (7) went from less than 1 μM to close to 1 mM. These experiments have been performed once with a fresh mixture DBCO-PEG4-NHS (7)/anti-PSA antibody and once with a 30 min old mixture. The measured difference in SPR signal between the functionalized surface (2') and the surface (2') after anti-PSA immobilization for each concentration for both type of mixtures are shown in FIG. 2 (plain circles for the fresh mixtures and hollow circles for the 30 min old mixtures). As can be seen in FIG. 2, the SPR signal was slightly better for the fresh mixture than for the 30 min old mixture. This suggests that the amount of anti-PSA that can be immobilized on the substrate is slightly higher if a fresh mixture is used. However, the SPR signal remains clearly good enough even for 30 min old mixtures. The stability of the mixture appears therefore good enough for wafer-level spotting. The degradation was further investigated using mixtures that had a longer lifetime and it was found that no significant decrease was measured when a 1.5 hours old mixture was used. So one can safely assume that the SPR signals would remain good enough even for older (e.g. two or three hours old mixtures). Furthermore, it can be observed that the use of a DBCO-PEG4-NHS (7) concentration lower than 1 μM give a SPR signal which is worse than our reference point while concentrations higher than 1 μM gave always at least a similar SPR signal and usually a better SPR signal than our reference point. This is indicative that if the concentration of DBCO-PEG4-NHS (7) is too low, the surface immobilization of the anti-PSA will be relatively low. What can also be derived from these experiments is that for most concentrations tested above 1 mM, even for 30 min old mixtures, the SPR signal was better than our reference point. This indicates that the amount of anti-PSA that can be immobilized on the substrate is at least equivalent and typically higher in the case of the present invention (when the DBCO-PEG4-NHS (7) and the anti-PSA are introduced as a mixture) than in the case of the prior art (when the DBCO-PEG4-NHS (7) is introduced first and the anti-PSA is introduced only later).

Figure 3:
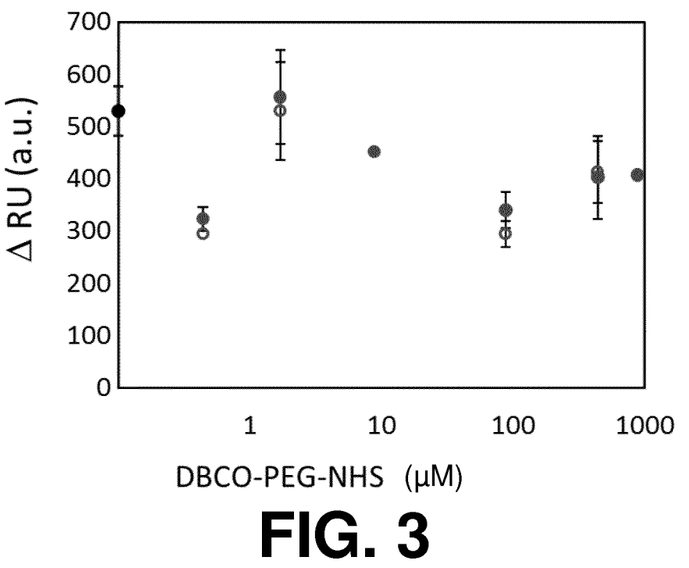
FIG. 3 is a graph of the SPR signal obtained after recognition of the analyte as a function of the coupling molecule concentration in embodiments of the present invention.

Now turning to FIG. 3. FIG. 3 shows on the Y-axis the difference in SPR signal measured before and after PSA recognition by the anti-PSA. A value around 550 a.u. was measured for the comparative two-step protocol. This value will be our reference point. In the one step protocol of the present invention (involving the immobilization of the anti-PSA via the use of a mixture DBCO-PEG4-NHS (7)/anti-PSA), the SPR signal was at least as good as the reference point for DBCO-PEG4-NHS (7) concentration higher than 1 µM but lower than 10 µM. Above 10 µM, the SPR signal was lower than our reference point but was still high enough to permit good PSA detection. This apparent drop in PSA recognition at 10 µM and above is presumably due to some degree of modification of the anti-PSA with multiple DBCO-PEG4-NHS molecules (7) that would be detrimental to recognition with PSA. Here also, the deterioration of the SPR signal observed when comparing the fresh mixtures with the 30 min old mixture indicates that a fresh mixture is typically better but that a 30 min old mixture is not much worse and that a mixture having one or even a few hours could still be used. From FIG. 2 and FIG. 3 we can already conclude that the one-step process toward anti-PSA immobilization of the present invention is a viable alternative to the two-step process of the prior art. This is important because the one-step process has the advantage over the prior art of only requiring one step of contacting the functionalized surface (2') with a single solution. Hence only one spot deposition is sufficient while the prior art requires two spot depositions steps, one on top of the other, which is not easy to implement in practice in a high throughput environment.

Figure 4:
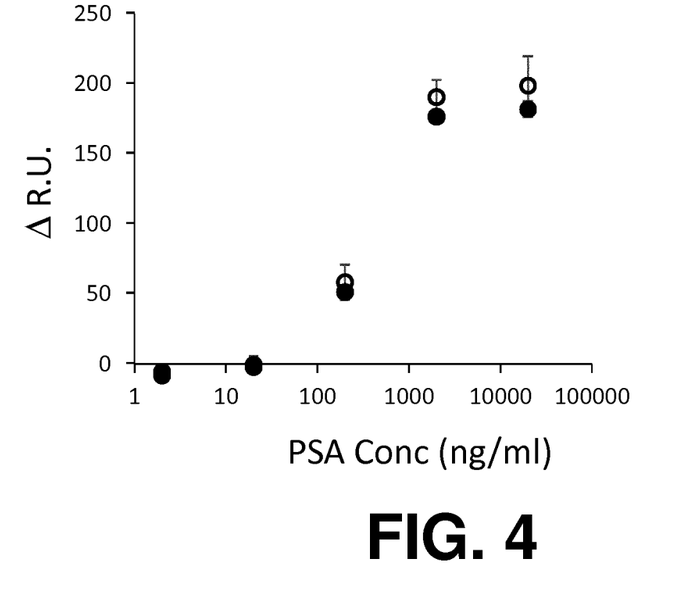
FIG. 4 is a graph of the SPR signal obtained after recognition of the analyte as a function of the analyte concentration according to embodiments of the present invention.

FIG. 4 shows experiments that have been conducted by using either the two step anti-PSA immobilization protocol of the prior art (empty circles) or the one step anti-PSA immobilization protocol of the present invention (full circles), as a function of the PSA concentration in the solution to be analysed. As can be seen, the SPR signal is almost identical for both the two steps protocol of the prior art and the one step protocol of the present invention.

Figure 5:
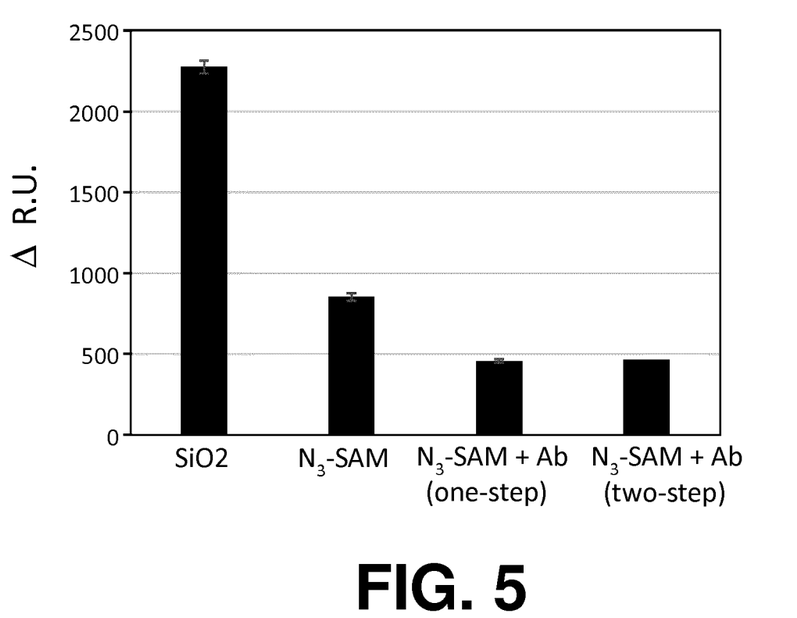
FIG. 5 is a graph comparing the SPR signal obtained after contacting of different surfaces with foetal bovine serum, one of the surface being prepared according to an embodiment of the present invention.

FIG. 5 shows the results of experiments that have been conducted to evaluate the degree of non-specific bonding of foetal bovine serum in function of the type of surface functionalization of the substrate. For a non-functionalized SiO2 surface (2), we observed a very large SPR signal at around 2300 a.u. due to non-specific bonding of foetal bovine serum. For the functionalized surface (2') bearing —$N_3$ groups, the SPR signal due to non-specific bonding of the foetal bovine serum was lower but still relatively high at around 800 a.u. For the surfaces (2') on which an anti-PSA is immobilized, whether via the two step method of the prior art or the one step method of the present invention, the SPR signal due to non-specific bonding of the foetal bovine serum was relatively low and of similar magnitude (around 450 a.u.). These results indicates that non-specific binding problems to immobilized analyte recognizing molecules are of a similar magnitude in the prior art and in the present invention.

Figure 6:
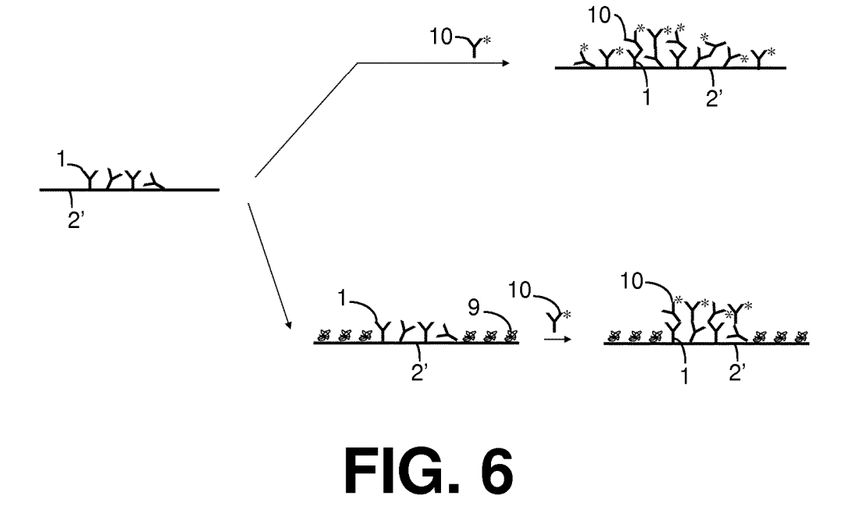
FIG. 6 is a schematic representation comparing the use of blocking agents with their non-use in embodiments of the present invention.

FIG. 6 shows schematically a strategy to reduce problems due to non-specific binding. Once the analyte-recognizing molecule (1) has been bound to the functionalized surface (2') via the coupling molecule (7), it is advantageous to block the parts of the surface which are free of analyte-recognizing molecule. This permits to avoid non-specific bounding of analytes away from the analyte-recognizing molecules. To achieve this, a blocking molecule can be deposited on the functionalized surface (2') after immobilization on that functionalized surface (2') of the analyte-recognizing molecule. On the left side of FIG. 6, the functionalized surface (2') with analyte-recognizing molecules immobilized thereon is shown. The right side of FIG. 6 shows the situation, with (bottom) or without (top) blocking, for a functionalized surface (2') on which analyte-recognizing molecules are immobilized and which has been contacted with the analyte. As can be seen in the top part of FIG. 6, non-specific binding of the analyte with the surface occur. As can be seen in the bottom part of FIG. 6, only specific binding by the analyte-recognizing molecules occur if a blocking agent has been used.

Figure 7:
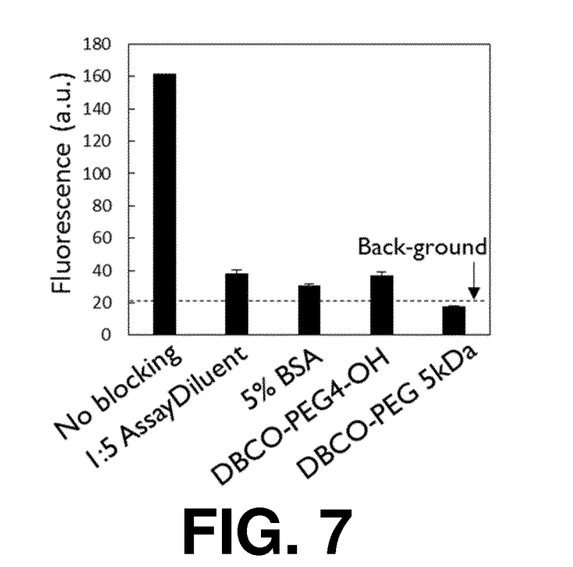
FIG. 7 is a graph of the fluorescence emitted by a fluorescent analyte as a function of the nature of the blocking agent used to cover a functionalized surface according to embodiments of the present invention.

FIG. 7 shows a graph of the fluorescence emitted by a fluorescent analyte as a function of the nature of the blocking agent used to cover a functionalized surface (2'). As can be seen, any blocking agent is much better than nothing and the best results (lower background fluorescence and therefore lower signal to noise ratio) were achieved with DBCO-PEG 5 kDa molecules (Jena Bioscience, Germany) wherein the DBCO part is the same as in the DBCO-PEG4-NHS molecules (7) and where the PEG 5 kDa is a polyethylene glycol having a molecular weight of about 5000 Da. The second best blocking agent was a 5% BSA solution.

Figure 8:
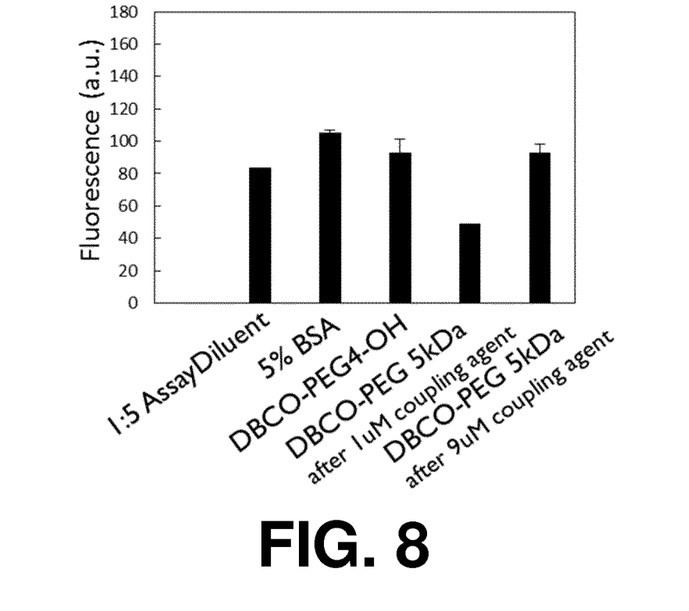
FIG. 8 is a graph of the fluorescence emitted by a fluorescent analyte as a function of the nature of the blocking agent used after immobilization of an analyte-recognizing molecule.

FIG. 8 shows a graph of the fluorescence emitted by a fluorescent analyte (Fluorescent Atto-647 IgG) as a function of the nature of the blocking agent used after immobilization of an analyte-recognizing molecule (1) (anti-IgG). To perform that experiment, a functionalized surface (2') was first contacted with a mixture analyte recognizing molecule (1)/DBCO-PEG4-NHS molecules (7) (at 9 µM in all but one case), then with a blocking agent, and finally with the analyte. As can be readily observed, fluorescence is at a similar level independently of the blocking agent used, except when the concentration of coupling molecule (7) in the mixture is at 1 µM. In that case, the fluorescence is inferior. This is indicative of the fact that a low coupling molecule (7) concentration during immobilization leads to a decrease in specific binding of the analyte.

In a further experiment, fluorescent antibodies have been spotted on a functionalized surface by using the method of the present invention. The $SiO_2$ surface was functionalized with a self-assembled monolayer comprising —$N_3$ groups. Different concentration of fluorescent IgG (functionalized with a Atto-647 fluorescent label) in a freshly prepared solution comprising DBCO-PEG4-NHS molecules (at 9 µM) in an acetate buffer at pH 5 were dropped on that functionalized surface. The resulting surface having fluorescent IgG immobilized thereon were then washed with a PBS buffer. The different fluorescent IgG concentrations tested were 3 µg/ml, 6 µg/ml, 12.5 µg/ml, 25 µg/ml, 50 µg/ml and 100 µg/ml. Two type of solutions were used. One type did not comprise a uniformity agent, the other type comprised betaïne 0.2 M as a uniformity agent. Fluorescence intensity was measured as a function of the position on the droplet. The within-droplet uniformity was good for both types of solution and especially so at high (50 µg/ml or higher) antibody concentration. The within-droplet uniformity was improved when betaïne was present, especially at lower antibody concentration.

In a further experiment, anti-IgG capture antibodies have been spotted on a functionalized surface by using the method of the present invention. The SiO$_2$ surface was functionalized with a self-assembled monolayer comprising —N$_3$ groups. Different concentration of anti-IgG capture antibodies in a freshly prepared solution comprising DBCO-PEG4-NHS molecules (at 9 µM) in an acetate buffer at pH 5 were dropped on that functionalized surface. A blocking step with BSA was then performed. Finally, a fluorescent IgG (functionalized with a Atto-647 fluorescent label) contacted with the surface having fluorescent IgG immobilized thereon. The different anti-IgG concentrations tested were 6 µg/ml, 12 µg/ml, 25 µg/ml, 50 µg/ml and 100 µg/ml. Two type of solutions were used. One type did not comprise a uniformity agent, the other type comprised betaïne 0.2 M as a uniformity agent. Fluorescence intensity was measured as a function of the position on the droplet. The within-droplet uniformity was good and especially so at high (50 µg/ml or higher) anti-IgG concentration. The presence of captured IgG could be detected by the corresponding fluorescence signal.

It is to be understood that although preferred embodiments, specific constructions and configurations, as well as materials, have been discussed herein for devices according to the present invention, various changes or modifications in form and detail may be made without departing from the scope of this invention. For example, any formulas given above are merely representative of procedures that may be used. Steps may be added or deleted to methods described within the scope of the present invention.

The invention claimed is:

1. A method for immobilizing an analyte-recognizing molecule on a functionalized surface, the method comprising the steps of:
   a) providing a surface functionalized with —N$_3$ groups; and
   b) contacting the functionalized surface with a solution comprising both:
      i) a coupling molecule having an alkyne group and a N-hydroxysuccinimide ester group and having the formula:

and
   ii) an analyte-recognizing molecule having an —NH$_2$ group,
   wherein the N-hydroxysuccinimide group of the coupling molecule reacts with the —NH$_2$ group of the analyte-recognizing molecule and the alkyne group of the coupling molecule reacts with an —N$_3$ group of the surface so as to immobilize the analyte-recognizing molecule onto the surface;
   wherein the solution comprises the coupling molecule at a concentration ranging from 1 µM to 1 mM; and
   wherein the solution comprising the analyte-recognizing molecule and the coupling molecule is prepared by mixing the analyte-recognizing molecule and the coupling molecule at most 30 minutes before step b.

2. The method according to claim 1, wherein step b comprises deposition on the functionalized surface of a drop of the solution.

3. The method according to claim 1, wherein the functionalized surface is coupled with a transducer for generating a readable signal output upon interaction of an analyte with the immobilized analyte-recognizing molecule.

4. The method according to claim 1, wherein subsequent to step b, further comprising contacting the functionalized surface with a blocking agent.

5. The method according to claim 4, wherein the blocking agent is DBCOPEG 5 KDa or 5% bovine serum albumin.

* * * * *